United States Patent
DiGioia, III et al.

(10) Patent No.: US 6,205,411 B1
(45) Date of Patent: *Mar. 20, 2001

(54) COMPUTER-ASSISTED SURGERY PLANNER AND INTRA-OPERATIVE GUIDANCE SYSTEM

(75) Inventors: Anthony M. DiGioia, III, Pittsburgh, PA (US); David A. Simon, Boulder, CO (US); Branislav Jaramaz; Michael K. Blackwell, both of Pittsburgh, PA (US); Frederick M. Morgan, Quincy; Robert V. O'Toole, Brookline, both of MA (US); Takeo Kanade, Pittsburgh, PA (US)

(73) Assignee: Carnegie Mellon University, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/189,914

(22) Filed: Nov. 12, 1998

Related U.S. Application Data

(63) Continuation-in-part of application No. 08/803,993, filed on Feb. 21, 1997, now Pat. No. 5,880,976.

(51) Int. Cl.[7] .............................. A61F 2/32; A61F 2/34; A61F 2/36
(52) U.S. Cl. .................. 703/11; 703/7; 623/19; 623/20; 623/21; 623/22
(58) Field of Search ................... 703/11, 7; 606/86, 606/89, 90, 91; 623/11, 16, 18, 19, 20, 21, 22, 23, 914

(56) References Cited

U.S. PATENT DOCUMENTS

| | | | |
|---|---|---|---|
| 4,341,220 | 7/1982 | Perry | 606/130 |
| 4,905,148 | 2/1990 | Crawford | 382/131 |
| 5,007,936 | 4/1991 | Woolson | 128/898 |
| 5,086,401 | 2/1992 | Glassman et al. | 700/259 |
| 5,141,512 | 8/1992 | Farmer et al. | 606/87 |
| 5,242,455 | 9/1993 | Skeens et al. | 606/130 |
| 5,251,127 | 10/1993 | Raab | 606/130 |
| 5,299,288 | 3/1994 | Glassman et al. | 700/245 |
| 5,305,203 | 4/1994 | Raab | 606/1 |
| 5,360,446 | 11/1994 | Kennedy | 128/898 |
| 5,383,454 | 1/1995 | Bucholz | 600/429 |

(List continued on next page.)

OTHER PUBLICATIONS

A. M. DiGioia, M.D., D. A. Simon, B. Jaramaz, M. Blackwell, F. Morgan, R. V. O'Toole, B. Colgan, E. Kischell, HipNav: Pre–operative Planning and Intra–operative Navigational Guidance for Acetabular Implant Placement in Total Hip Replacement Surgery, Proceeding of Computer Assisted Orthopedic Surgery, Bern, Switzerland (1996).

Robert J. Krushell, M.D., Denis W. Burke, M.D. and William H. Harris, M.D., Range of Motion in Contemporary Total Hip Arthroplasty, pp. 97–101, The Journal of Arthroplasty, vol. 6, No. 2, Jun. 1991.

Robert J. Krushell, M.D., Dennis w. Burke, M.D. and William H. Harris, M.D., Elevated–rim Acetabular Components, pp. 1–6, The Journal of Arthroplasty, vol. 6, Oct., 1991.

(List continued on next page.)

Primary Examiner—Kevin J. Teska
Assistant Examiner—Russell W. Frejd
(74) Attorney, Agent, or Firm—Kirkpatrick & Lockhart LLP

(57) ABSTRACT

An apparatus for facilitating the implantation of an artificial component in one of a hip joint, a knee joint, a hand and wrist joint, an elbow joint, a shoulder joint, and a foot and ankle joint. The apparatus includes a pre-operative geometric planner and a pre-operative kinematic biomechanical simulator in communication with the pre-operative geometric planner.

17 Claims, 14 Drawing Sheets

U.S. PATENT DOCUMENTS

| | | | |
|---|---|---|---|
| 5,389,101 | | 2/1995 | Heilbrun et al. ................. 606/130 |
| 5,408,409 | | 4/1995 | Glassman et al. ................ 600/407 |
| 5,517,990 | | 5/1996 | Kalfas et al. .................... 600/414 |
| 5,682,886 | | 11/1997 | Delp et al. ....................... 600/407 |
| 5,733,338 | | 3/1998 | Kampner .......................... 128/898 |
| 5,880,976 | * | 3/1999 | DiGioia, III et al. ................ 703/7 |
| 5,995,738 | * | 11/1999 | DiGioia, III et al. .............. 703/11 |
| 6,002,859 | * | 12/1999 | DiGioia, III et al. .............. 703/11 |

OTHER PUBLICATIONS

George E. Lewinnek, M.D., Jack L. Lewis, Ph.D., Richard Tarr, M.S., Clinton L. Compere, M.D. and Jerald R. Zimmerman, B.S., Dislocations After Total Hip–Replacement Arthroplasties, pp. 217–220, vol. 60–A, No. 2, Mar., 1978, The Journal of Bone and Joint Surgery, Incorporated.

Harlan C. Amstutz, M.D., R. M. Lodwig, D. J. Schurman, M.D. and A. G. Hodgson, Range of Motion Studies for Total Hip Replacements, pp. 124–130, Clinical Orthopaedics and Related Research, #111, Sep., 1975.

T. K. Cobb, M.D., B. F. Morrey, M.D. and D. M. Ilstrup, M.S., The Elevated–Rim Acetabular Liner in Total Hip Arthroplasty: Relationship to Postoperative Dislocation, pp. 80–86, The Journal of Bone and Joint Surgery, 1996.

D. A. Simon, R. V. O'Toole, M. Blackwell, F. Morgan, A. M. DiGioia and T. Kanade, Accuracy Validation in Image–Guided Orthopaedic Surgery, $2^{nd}$ Annual Symposium on Medical Robotics and Computer Assisted Surgery, Baltimore, MD, Nov. $4-7^{th}$, 1995.

David A. Simon, Martial Hebert and Takeo Kanade, Techniques for Fast and Accurate Intrasurgical Registration, Journal of Image Guided Surgery, 1:17–29 (1995.).

Donald E. McCollum, M.D. and William J. Gray, M.D., Dislocation After Total Hip Arthroplasty, pp. 159–170, Clinical Orthopaedics and Related Research, No. 261, Dec., 1990.

David A. Simon, Martial Hebert and Takeo Kanade, Real–time 3–D Pose Estimation Using a High–Speed Range Sensor, pp. 1–14, Carnegie Mellon University, Robotics Institute, Technical Report, CMU–RI–TR–93–24, Nov., 1993.

T. A. Maxian, T. D. Brown, D. R. Pedersen, J. J. Callaghan, Femoral Head Containment in Total Hip Arthroplasty: Standard vs. Extended Lip Liners, p. 420, $42^{nd}$ Annual Meeting, Orthopaedic Research Society, Feb. 19–22, Atlanta, Georgia.

T. A. Maxian, T. D. Brown, D. R. Pederson and J. J. Callaghan, Finite Element Modeling of Dislocation Propensity in Total Hip Arthroplasty, p. 259–44, $42^{nd}$ Annual Meeting, Orthopaedic Research Society, Feb. 19–22, 1996, Atlanta, Georgia.

Vincent Dessenne, Stephane Lavallee, Remi Julliard, Rachel Orti, Sandra Martelli, Philippe Cinquin, , Computer–Assisted Knee Anterior Cruciate Ligament Reconstruction: First Clinical Tests, Journal of Image Guided Surgery 1:59–64 (1995).

Ali Hamadeh, Stephane Lavallee, Richard Szeliski, Philippe Cinquin, Olivier Peria, Anatomy–based Registration for Computer–integrated Surgery, pp. 212–218, Program of $1^{st}$ International Conference on Computer Version Virtual Reality "Robotics in Medicine" 1995, Nice, France.

K. Rademacher, H. W. Staudte, G. Rau, Computer Assisted Orthopedic Surgery by Means of Individual Templates Aspects and Analysis of Potential Applications, pp. 42–48.

Lutz–P. Nolte, Lucia J. Zamorano, Zhaowei Jiang, Qinghai Wang, Frank Langlotz, Erich Arm, Heiko Visarius, A Novel Approach to Computer Assisted Spine Surgery, pp. 323–328.

Robert Rohling, Patrice Munger, John M. Hollerbach, Terry Peters, Comparison of Relative Accuracy Between a Mechanical and an Optical Position Tracker for Image–Guided Neurosurgery, Journal of Image Guided Surgery, 1:30–34 (1995).

E. Grimson, T. Lozano–Perez, W. Wells, G. Ettinger, S. White, R. Kikinis, Automated Registration for Enhanced Reality Visualization in Surgery, pp. 26–29.

S. Lavalle, P. Sautot, J.Troccaz, P. Cinquin, P. Merloz, Computer–Assisted Spine Surgery: A Technique for Accurate Transpedicular Screw Fixation Using CT Data and a 3–D Optical Localizer, Journal of Image Guided Surgery 1:65–73 (1995).

Russell H. Taylor, Brent D. Mittelstadt, Howard A. Paul, William Hanson, Peter Kazanzides, Joel F. Zuhars, Bill Williamson, Bela L. Musits, Edward Glassman, William. L. Bargar, An Image–Directed Robotic System for Precise Orthopaedic Surgery, IEEE Transactions on Robotics and Automation, vol. 10, No. 3, Jun., 1994.

* cited by examiner

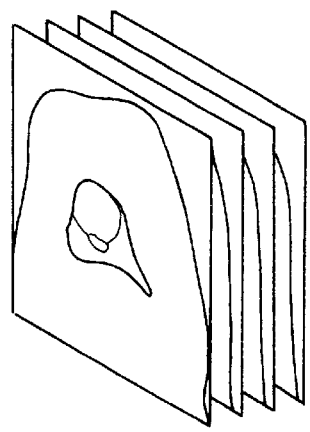
FIG. 4c
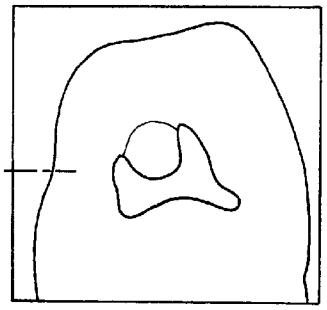
FIG. 4b
FIG. 4a

COMPUTER-ASSISTED SURGERY PLANNER AND INTRA-OPERATIVE GUIDANCE SYSTEM

CROSS-REFERENCE TO RELATED APPLICATIONS

This application is a continuation-in-part application of application Ser. No. 08/803,993, filed Feb. 21, 1997.

STATEMENT REGARDING FEDERALLY SPONSORED RESEARCH OR DEVELOPMENT

This work was supported in part by a National Challenge grant from the National Science Foundation Award IRI 9422734.

BACKGROUND OF THE INVENTION

The present invention is directed generally to the implantation of artificial joint components, osteochondral grafts, and osteotomy and, more particularly, to computer assisted surgical implantation of artificial joint components during replacement and revision procedures, computer-assisted osteochondral grafts, and computer-assisted osteotomy.

Total hip replacement (THR) or arthroplasty (THA) operations have been performed since the early 1960s to repair the acetabulum and the region surrounding it and to replace the hip components, such as the femoral head, that have degenerated. Currently, approximately 200,000 THR operations are performed annually in the United States alone, of which approximately 40,000 are redo procedures, otherwise known as revisions. The revisions become necessary due to a number of problems that may arise during the lifetime of the implanted components, such as dislocation, component wear and degradation, and loosening of the implant from the bone.

Dislocation of the femoral head from the acetabular component, or cup, is considered one of the most frequent early problems associated with THR, because of the sudden physical, and emotional, hardship brought on by the dislocation. The incidence of dislocation following the primary THR surgery is approximately 2–6% and the percentage is even higher for revisions. While dislocations can result from a variety of causes, such as soft tissue laxity and loosening of the implant, the most common cause is impingement of the femoral neck with either the rim of an acetabular cup implant, or the soft tissue or bone surrounding the implant. Impingement most frequently occurs as a result of the malposition of the acetabular cup component within the pelvis.

Some clinicians and researchers have found incidence of impingement and dislocations can be lessened if the cup is oriented specifically to provide for approximately 15° of anteversion and 45° of abduction; however, this incidence is also related to the surgical approach. For example, McCollum et al. cited a comparison of THAs reported in the orthopaedic literature that revealed a much higher incidence of dislocation in patients who had THAs with a posterolateral approach. McCollum, D. E. and W. J. Gray, "Dislocation after total hip arthroplasty (causes and prevention)", Clinical Orthopaedics and Related Research, Vol. 261, p.159–170 (1990). McCollum's data showed that when the patient is placed in the lateral position for a posterolateral THA approach, the lumbar lordotic curve is flattened and the pelvis may be flexed as much as 35°. If the cup was oriented at 15–20° of flexion with respect to the longitudinal axis of the body, when the patient stood up and the postoperative lumbar lordosis was regained, the cup could be retroverted as much as 10°–15° resulting in an unstable cup placement. Lewinnek et al. performed a study taking into account the surgical approach utilized and found that the cases falling in the zone of 15°±10° of anteversion and 40°±10° of abduction have an instability rate of 1.5%, compared with a 6% instability rate for the cases falling outside this zone. Lewinnek G. E., et al., "Dislocation after total hip-replacement arthroplasties", Journal of Bone and Joint Surgery, Vol. 60-A, No.2, p. 217–220 (March 1978). The Lewinnek work essentially verifies that dislocations can be correlated with the extent of malpositioning, as would be expected. The study does not address other variables, such as implant design and the anatomy of the individual, both of which are known to greatly affect the performance of the implant.

The design of the implant significantly affects stability as well. A number of researchers have found that the head-to-neck ratio of the femoral component is the key factor of the implant impingement, see Amstutz H. C., et al., "Range of Motion Studies for Total Hip Replacements", Clinical Orthopaedics and Related Research Vol. 111, p. 124–130 (September 1975). Krushell et al. additionally found that certain long and extra long neck designs of modular implants can have an adverse effect on the range of motion. Krushell, R. J., Burke D. W., and Harris W. H., "Range of motion in contemporary total hip arthroplasty (the impact of modular head-neck components)", The Journal of Arthroplasty, Vol. 6, p. 97–101 (February 1991). Krushell et al. also found that an optimally oriented elevated-rim liner in an acetabular cup implant may improve the joint stability with respect to implant impingement. Krushell, R. J., Burke D. W., and Harris W. H., "Elevated-rim acetabular components: Effect on range of motion and stability in total hip arthroplasty", The Journal of Arthroplasty, Vol. 6 Supplement, p. 1–6, (October 1991). Cobb et al. have shown a statistically significant reduction of dislocations in the case of elevated-rim liners, compared to standard liners. Cobb T. K., Morrey B. F., Ilstrup D. M., "The elevated-rim acetabular liner in total hip arthroplasty: Relationship to postoperative dislocation", Journal of Bone and Joint Surgery, Vol 78-A, No. 1, p. 80–86, (January 1996). The two-year probability of dislocation was 2.19% for the elevated liner, compared with 3.85% for standard liner. Initial studies by Maxian et al. using a finite element model indicate that the contact stresses and therefore the polyethylene wear are not significantly increased for elevated rim liners; however, points of impingement and subsequent angles of dislocation for different liner designs are different as would be expected. Maxian T. A., et al. "Femoral head containment in total hip arthroplasty: Standard vs. extended lip liners", 42nd Annual meeting, Orthopaedic Research society, p. 420, Atlanta, Ga. (Feb. 19–22, 1996); and Maxian T. A., et al. "Finite element modeling of dislocation propensity in total hip arthroplasty", 42nd Annual meeting, Orthopaedic Research society, p. 259–64, Atlanta, Ga. (Feb. 19–22, 1996).

An equally important concern in evaluating the dislocation propensity of an implant are variations in individual anatomies. As a result of anatomical variations, there is no single optimal design and orientation of hip replacement components and surgical procedure to minimize the dislocation propensity of the implant. For example, the pelvis can assume different positions and orientations depending or whether an individual is lying supine (as during a CT-scan or routine X-rays), in the lateral decubitis position (as during surgery) or in critical positions during activities of normal daily living (like bending over to tie shoes or during normal gait). The relative position of the pelvis and leg when defining a "neutral" plane from which the angles of movement, anteversion, abduction, etc., are calculated will significantly influence the measured amount of motion permitted before impingement and dislocation occurs. Therefore, it is necessary to uniquely define both the neutral orientation of the femur relative to the pelvis for relevant positions and activities, and the relations between the femur with respect to the pelvis of the patient during each segment of leg motion.

Currently, most planning for acetabular implant placement and size selection is performed using acetate templates and a single anterior-posterior x-ray of the pelvis. Acetabular templating is most useful for determining the approximate size of the acetabular component; however, it is only of limited utility for positioning of the implant because the x-rays provide only a two dimensional image of the pelvis. Also, the variations in pelvic orientation can not be more fully considered as discussed above.

Intra-operative positioning devices currently used by surgeons attempt to align the acetabular component with respect to the sagittal and coronal planes of the patient. B. F. Morrey, editor, "Reconstructive Surgery of the Joints", chapter Joint Replacement Arthroplasty, pages 605–608, Churchill Livingston, 1996. These devices assume that the patient's pelvis and trunk are aligned in a known orientation, and do not take into account individual variations in a patient's anatomy or pelvic position on the operating room table. These types of positioners can lead to a wide discrepancy between the desired and actual implant placement, possibly resulting in reduced range of motion, impingement and subsequent dislocation.

Several attempts have been made to more precisely prepare the acetabular region for the implant components. U.S. Pat. No. 5,007,936 issued to Woolson is directed to establishing a reference plane through which the acetabulum can be reamed and generally prepared to receive the acetabular cup implant. The method provides for establishing the reference plane based on selecting three reference points, preferably the 12 o'clock position on the superior rim of the acetabulum and two other reference points, such as a point in the posterior rim and the inner wall, that are a known distance from the superior rim. The location of the superior rim is determined by performing a series of computed tomography (CT) scans that are concentrated near the superior rim and other reference locations in the acetabular region.

In the Woolson method, calculations are then performed to determine a plane in which the rim of the acetabular cup should be positioned to allow for a predetermined rotation of the femoral head in the cup. The distances between the points and the plane are calculated and an orientation jig is calibrated to define the plane when the jig is mounted on the reference points. During the surgical procedure, the surgeon must identify the 12 o'clock orientation of the superior rim and the reference points. In the preferred mode, the jig is fixed to the acetabulum by drilling a hole through the reference point on the inner wall of the acetabulum and affixing the jig to the acetabulum. The jig incorporates a drill guide to provide for reaming of the acetabulum in the selected plane.

A number of difficulties exist with the Woolson method. For example, the preferred method requires drilling a hole in the acetabulum. Also, visual recognition of the reference points must be required and precision placement on the jig on reference points is performed in a surgical setting. In addition, proper alignment of the reaming device does not ensure that the implant will be properly positioned, thereby establishing a more lengthy and costly procedure with no guarantees of better results. These problems may be a reason why the Woolson method has not gained widespread acceptance in the medical community.

In U.S. Pat. Nos. 5,251,127 and 5,305,203 issued to Raab, a computer-aided surgery apparatus is disclosed in which a reference jig is attached to a double self indexing screw, previously attached to the patient, to provide for a more consistent alignment of the cutting instruments similar to that of Woolson. However, unlike Woolson, Raab et al. employ a digitizer and a computer to determine and relate the orientation of the reference jig and the patient during surgery with the skeletal shapes determined by tomography.

Similarly, U.S. Pat. Nos. 5,086,401, 5,299,288 and 5,408, 409 issued to Glassman et al. disclose an image directed surgical robotic system for reaming a human femur to accept a femoral stem and head implant using a robot cutter system. In the system, at least three locating pins are inserted in the femur and CT scans of the femur in the region containing the locating pins are performed. During the implanting procedure, the locating pins are identified on the patient, as discussed in col. 9, lines 19–68 of Glassman's '401 patent. The location of the pins during the surgery are used by a computer to transform CT scan coordinates into the robot cutter coordinates, which are used to guide the robot cutter during reaming operations.

While the Woolson, Raab and Glassman patents provide methods and apparatuses that further offer the potential for increased accuracy and consistency in the preparation of the acetabular region to receive implant components, there remain a number of difficulties with the procedures. A significant shortcoming of the methods and apparatuses is that when used for implanting components in a joint there are underlying assumptions that the proper position for the placement of the components in the joints has been determined and provided as input to the methods and apparatuses that are used to prepare the site. As such, the utility and benefit of the methods and apparatuses are based upon the correctness and quality of the implant position provided as input to the methods.

In addition, both the Raab and Glassman methods and apparatuses require that fiducial markers be attached to the patient prior to performing tomography of the patients. Following the tomography, the markers must either remain attached to the patient until the surgical procedure is performed or the markers must be reattached at the precise locations to allow the transformation of the tomographic data to the robotic coordinate system, either of which is undesirable and/or difficult in practice.

Thus, the need exists for apparatuses and methods which overcome, among others, the above-discussed problems so as to provide for the proper placement and implantation of the joint components to provide an improved range of motion and usage of the joint following joint reconstruction, replacement and revision surgery.

BRIEF SUMMARY OF THE INVENTION

The present invention is directed to an apparatus for facilitating the implantation of an artificial component in one of a hip joint, a knee joint, a hand and wrist joint, an elbow joint, a shoulder joint, and a foot and ankle joint. The apparatus includes a pre-operative geometric planner and a pre-operative kinematic biomechanical simulator in communication with the pre-operative geometric planner.

The present invention provides the medical practitioner a tool to precisely determine an optimal size and position of artificial components in a joint to provide a desired range of motion of the joint following surgery and to substantially lessen the possibility of subsequent dislocation. Accordingly, the present invention provides an effective solution to problems heretofore encountered with precisely determining the proper sizing and placement of an artificial component to be implanted in a joint. In addition, the practitioner is afforded a less invasive method for executing the surgical procedure in accordance with the present invention. These advantages and others will become apparent from the following detailed description.

BRIEF DESCRIPTION OF THE DRAWINGS

A preferred embodiment of the invention will now be described, by way of example only, with reference to the accompanying figures wherein like members bear like reference numerals and wherein:

FIGS. 4(a–c) show the creation of the pelvic model using two dimensional scans of the pelvis (a), from which skeletal geometric data is extracted as shown in (b) and used to create the pelvic model (c);

DETAILED DESCRIPTION OF THE INVENTION

Figure 1:
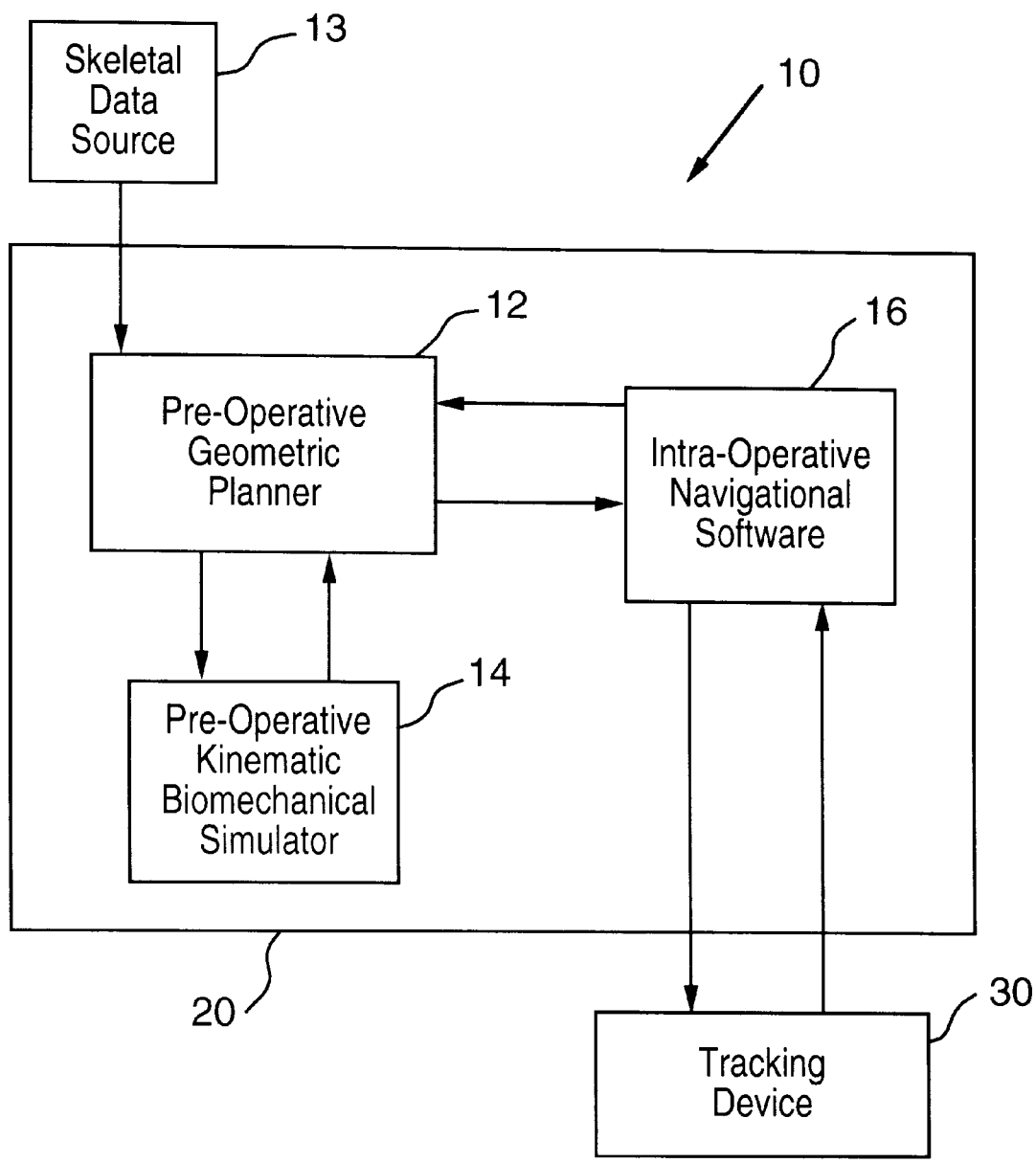
FIG. 1 is a system overview of a preferred embodiment of the present invention.

The apparatus 10 of the present invention will be described generally with reference to the drawings for the purpose of illustrating the present preferred embodiments of the invention only and not for purposes of limiting the same. A system overview is provided in FIG. 1 and general description of the method of the present invention is presented in flow chart form in FIG. 2. The apparatus 10 includes a geometric pre-operative planner 12 that is used to create geometric models of the joint and the components to be implanted based on geometric data received from a skeletal structure data source 13. The pre-operative planner 12 is interfaced with a pre-operative kinematic biomechanical simulator 14 that simulates movement of the joint using the geometric models for use in determining implant positions, including angular orientations, for the components. The implant positions are used in conjunction with the geometric models in intra-operative navigational software 16 to guide a medical practitioner in the placement of the implant components at the implant positions.

Figure 3:
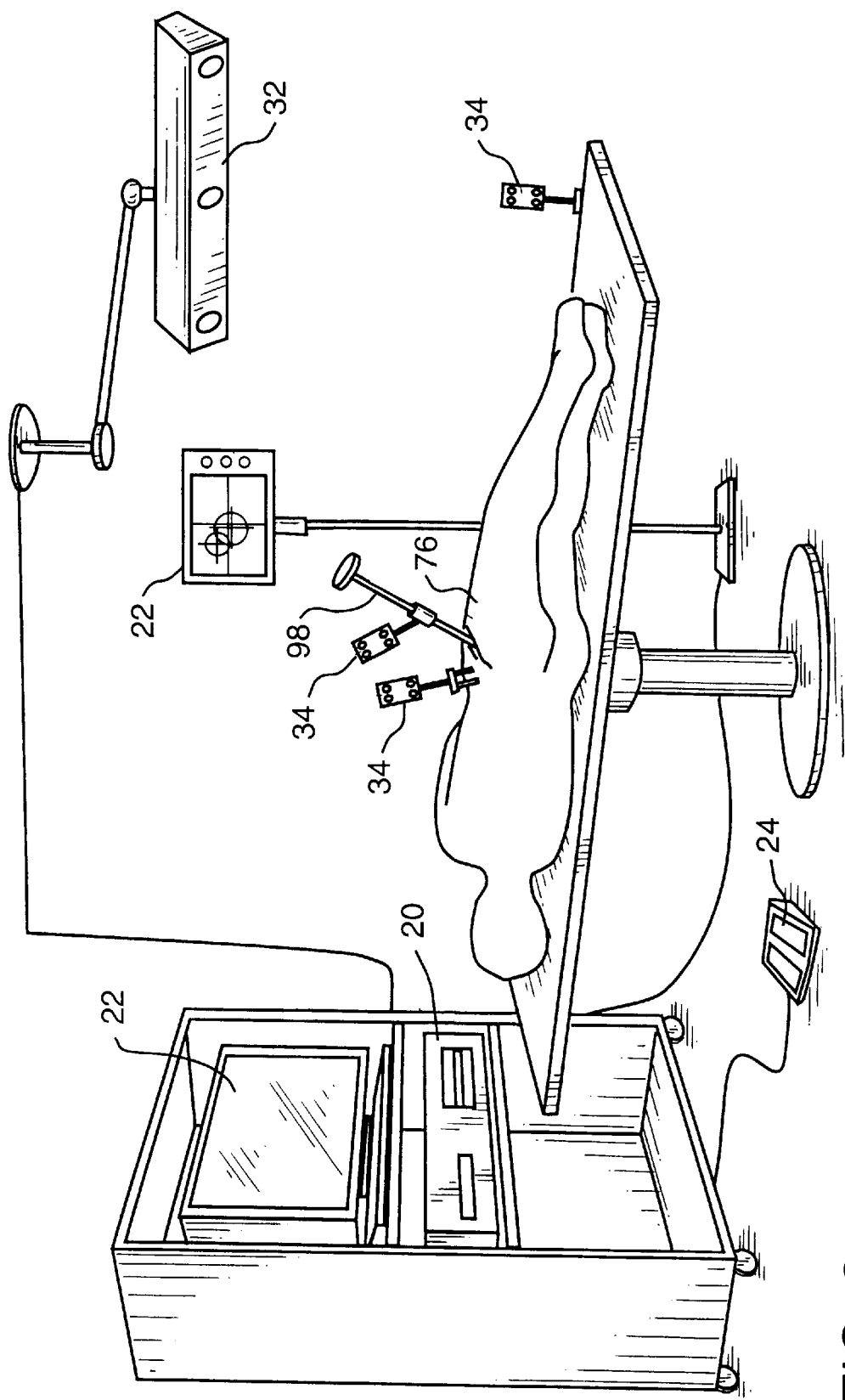
FIG. 3 is a schematic layout of the apparatus of the present invention being used in a hip replacement procedure.

The pre-operative geometric planner 12, the pre-operative kinematic biomechanical simulator 14 and the intra-operative navigational software are implemented using a computer system 20 having at least one display monitor 22, as shown in FIG. 3. For example, applicants have found that a Silicon Graphics O2 workstation (Mountain View, Calif.) can be suitably employed as the computer system 20; however, the choice of computer system 20 will necessarily depend upon the resolution and calculational detail sought in practice. During the pre-operative stages of the method, the display monitor 22 is used for viewing and interactively creating and/or generating models in the pre-operative planner 12 and displaying the results of the biomechanical simulator 14. The pre-operative stages of the method may be carried out on a computer (not shown) remote from the surgical theater.

During the intra-operative stages of the method, the computer system 20 is used to display the relative locations of the objects being tracked with a tracking device 30. The medical practitioner preferably can control the operation of the computer system 20 during the procedure, such as through the use of a foot pedal controller 24 connected to the computer system 20. The tracking device 30 can employ any type of tracking method as may be known in the art, for example, emitter/detector systems including optic, acoustic or other wave forms, shape based recognition tracking algorithms, or video-based, mechanical, electromagnetic and radio frequency (RF) systems. In a preferred embodiment, schematically shown in FIG. 3, the tracking device 30 is an optical tracking system that includes at least one camera 32 that is attached to the computer system 20 and positioned to detect light emitted from a number of special light emitting diodes, or targets 34. The targets 34 can be attached to bones, tools, and other objects in the operating room equipment to provide precision tracking of the objects. One such device that has been found to be suitable for performing the tracking function is the Optotrak™ 3020 system from Northern Digital Inc., Ontario, Canada, which is advertised as capable of achieving accuracies of roughly 0.1 mm at speeds of 100 measurements per second or higher.

Figure 2:
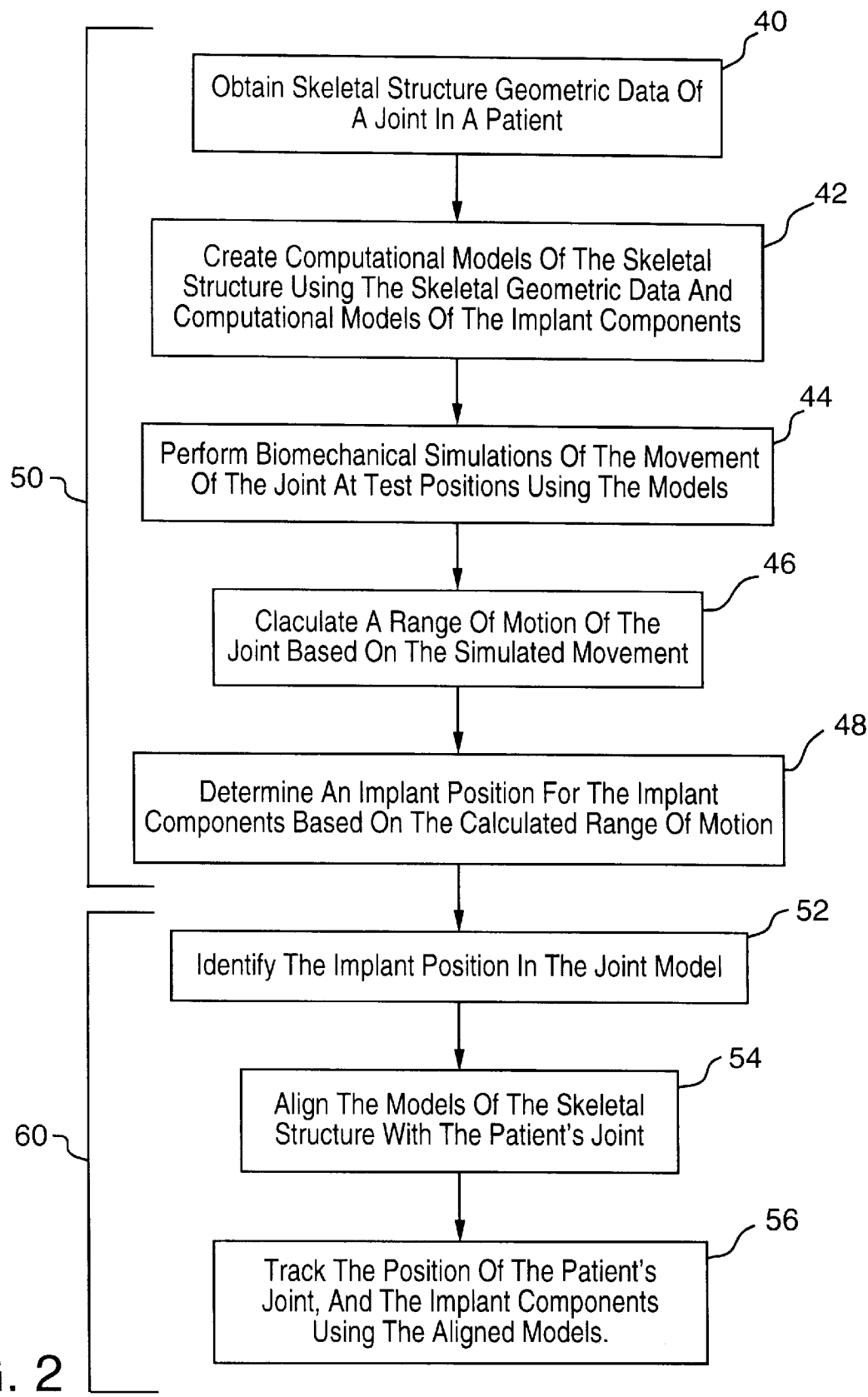
FIG. 2 is a flow chart illustrating the method of the present invention.

The apparatus 10 of FIG. 1 is operated in accordance with the method illustrated in FIG. 2. The skeletal structure of the joint is determined at step 40 using tomographic data (three dimensional) or computed tomographic data (pseudo three dimensional data produced from a series of two dimensional scans) or other techniques from the skeletal data source 13. Commonly used tomographic techniques include computed tomography (CT), magnetic resonance imaging (MRI), positron emission tomographic (PET), or ultrasound scanning of the joint and surround structure. The tomographic data from the scanned structure generated by the skeletal data source 13 is provided to the geometric planner 12 for use in producing a model of the skeletal structure. It should be noted that, in a preferred embodiment, there is no requirement that fiducial markers be attached to the patient in the scanned region to provide a reference frame for relating the tomography scans to intra-operative position of the patient, although markers can be used as a cross reference or for use with other alternative embodiments.

At step 42, a surface model is created, or constructed, from the skeletal geometric data using techniques, such as those described by B. Geiger in "Three-dimensional modeling of human organs and its application to diagnosis and surgical planning", Ph.D. thesis, Ecole des Mines de Paris, April 1993. The geometric models constructed from the skeletal data source 13 can be manually generated and input to the geometric planner 12, but it is preferable that the data be used to create the geometric models in an automated fashion.

Also at step 42, geometric models of the artificial components to be implanted into the joint are created/generated. The geometric models can be created in any manner as is known in the art including those techniques described for creating joint models. The geometric models of the artificial components can be used in conjunction with the joint model to determine an initial static estimate of the proper size of the artificial components to be implanted.

In step 44, the geometric models of the joint and the artificial components are used to perform biomechanical simulations of the movement of the joint containing the implanted artificial components. The biomechanical simulations are preferably performed at a number of test positions to dynamically optimize the size, position and orientation of the artificial components in the patient's joint to achieve a predetermined range of motion following surgery. The predetermined range of motion for a particular patient is determined based on the expected activities of the patient following surgery. For example, with regard to hip functions, daily activities, such as getting out of bed, walking, sitting and climbing stairs, that are performed by individuals requiring different ranges of motion, as will be discussed in further detail below.

The size and orientations of the implant component, and movements simulated at various test positions used in step 44 can be fully automated or manually controlled. In a preferred embodiment, the selection and test process would be automated so as to be more fully optimizable to a predetermined range of motion, either generally, or for predetermined activity. However, because it is necessary that medical practitioners be comfortable and develop confidence in the system, manual control is provided over the selection of the implant components and the test positions in the biomechanical simulator 14.

In step 46, the simulated movement of the joint at various implant positions is used to calculate a range of motion for each implant position. In step 48, the calculated ranges of motion are compared to the predetermined range of motion to select an implant position for the artificial components. A goal of the simulation process is to find the implant position which optimizes the calculated range of motion using the predetermined range of motion as a basis for optimization. In practice, the predetermined range of motion is determined based on desired functional motions selected by a medical practitioner on a patient specific basis (e.g. sitting requires flexion of 90°). The determination of the implant position can be further influenced by others factors such as the variation in the calculated range of motion as a function of implant component orientation. This criterion is useful for determining the surgical margin of error that is available to the medical practitioner without a substantial diminution in the range of motion of the joint.

Steps 40, 42, 44, 46 and 48 represent a pre-operative procedure 50 which is performed so that the artificial components can be properly sized and implant positions can be properly determined. The remainder of the steps in FIG. 2, steps 52, 54, and 56 comprise a procedure 60 which enables a surgeon to realize the desired implant position in the surgical theater.

In step 52, the implant positions determined using procedure 50 are then identified, by marking or incorporating the information in some appropriate manner in the geometric model of the joint. The geometric models of the joint and the artificial components can then be used in conjunction with positional data obtained from the joint and the artificial components during a surgical procedure to provide intra-operative guidance for the implantation of the artificial components.

In step 54, the joint model based on the skeletal data is aligned with the intra-operative position of the patient's joint. In a preferred embodiment, step 54 is performed using a technique known as three dimensional (3D) surface registration. In 3D surface registration, discrete registration points are obtained from the joint skeletal structure to define the intra-operative position of the patient's joint. The registration points are fitted to the joint model of the skeletal structure to determine a coordinate transformation that is used to align the joint model with the intra-operative position of the patient's joint. Once the transformation is established, the intra-operative position of the patient's joint can be tracked using the joint model by obtaining positional data from a point on the joint that provides spatial correspondence between the pre-operative models and the intra-operative measurements. A more thorough description of the surface registration procedure is discussed in D. A. Simon, M. Hebert, and T. Kanade, "Real-time 3-D Pose Estimation Using a High-Speed Range Sensor", Carnegie Mellon University, Robotics Institute Technical Report CMU-RI-TR-93-24 (November 1993); D. A. Simon, M. Hebert, and T. Kanade, "Techniques for fast and accurate intra-surgical registration", Journal of Image Guided Surgery, 1(1):17–29, (April 1995); and D. A. Simon, et al., "Accuracy validation in image-guided orthopaedic surgery", Proc. 2nd Int'l Symp. MRCAS, Baltimore, (November 1995), which are incorporated herein by reference.

The physical location of the intra-operative registration points on the joint from which the positional data is obtained will determine the amount of positional data required to uniquely determine and align the geometric model with the registration points. For example, it is desirable to obtain positional data from the joint that will maximize the constraint on the possible solutions to the alignment problem and provide high level of sensitivity to variations in the position, including orientation, of the joint, as discussed above in the Simon et al. references. The goal of the registration process is to determine a "registration transformation" which best aligns the discrete points that provide the spatial position and orientation of the joint with the joint models. Preferably, an initial estimate of this transformation is first determined using manually specified anatomical landmarks to perform corresponding point registration. Once this initial estimate is determined, the surface-based registration algorithm uses the pre- and intra-operative data to refine the initial transformation estimate.

Figure 3A:
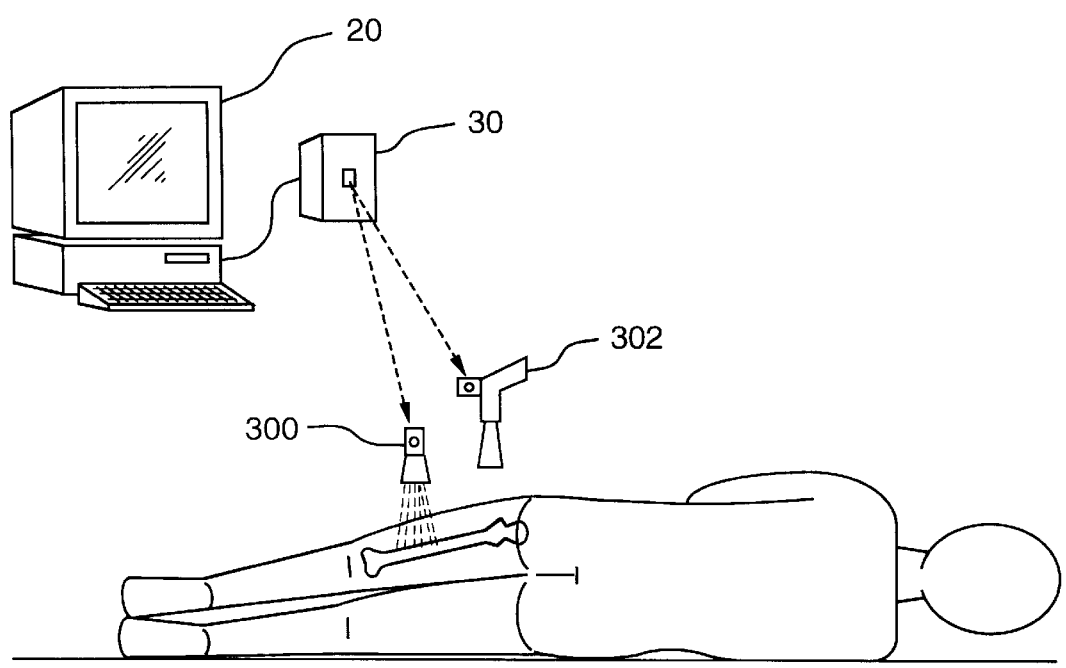
FIG. 3A is a diagram illustrating an embodiment of a system which can be used to find the coordinates of points on a bony surface.

As illustrated in FIG. 3A, the coordinates of the points on the bony surface can be found using a sensing device 300 such as, for example, a pointing probe, an ultrasound probe, a fluoroscopic imaging device, an optical range sensor, or a mechanical arm. The sensing device 300 is used to measure the positions of discrete points on the bony surface relative to the sensing device 300. The position of the sensing device 300 is tracked using the tracking device 30. Thus, the position of the discrete points on the bony surface can be expressed relative to the tracking device 30, and then registered with the pre-operative plan. The position of a surgical tool 302 can also be tracked intra-operatively by the tracking device 30.

Alternatively, step 54 can be implemented using registration systems that employ fiducial markers, to align the pre-operative data with the intra-operative position of the patient's joint. In those methods, the fiducial markers must be surgically implanted into the skeletal structure before pre-operative images are acquired in step 40. The intra-operative position of the fiducial markers are compared to the pre-operative data to determine the position of the patient's joint. An example of such a fiducial marker system is discussed in R. H. Taylor, et al., "An image-directed robotic system for precise orthopaedic surgery", IEEE Trans. on Robotics and Automation, 10(3):261–275, June 1994. In addition, step 54 can be implemented using other registration systems that do not require the pre-operative use of fiducial markers.

In step 56, the position of the joint and the implant components are tracked and compared in near real time to the implant position identified in the joint model. In this step, the tracking device 30 provides the positional data representative of the position of the patient's joint to the computer system 20. The computer system 20 employs registration routines within the intra-operative navigational software 16 to determine the position and orientation of the joint and then displays the relative positions of the artificial component and the implant position. The tracking device 30 can also be used to track and provide positional data representative of the position of other physical objects in the operating room, such as surgical instruments. Additional details of the methods and apparatuses are presented in "HipNav: Pre-operative Planning and Intra-operative Navigational Guidance for Acetabular Implant Placement in Total Hip Replacement Surgery". DiGioia et al., $2^{nd}$ CAOS Symposium, Bern, Switzerland, 1996, which is incorporated herein by reference.

The pre-operative procedure 50 and the alignment step 54 provide a way to define the space within which surgical tools can be moved safely. If a surgical tool is attached to a robotic arm and is tracked at step 56, the robotic arm can limit movement of the tool to staying within the defined space. Thus, surgical cuts can be made freely but within precise spatial constraints.

Figure 5C:
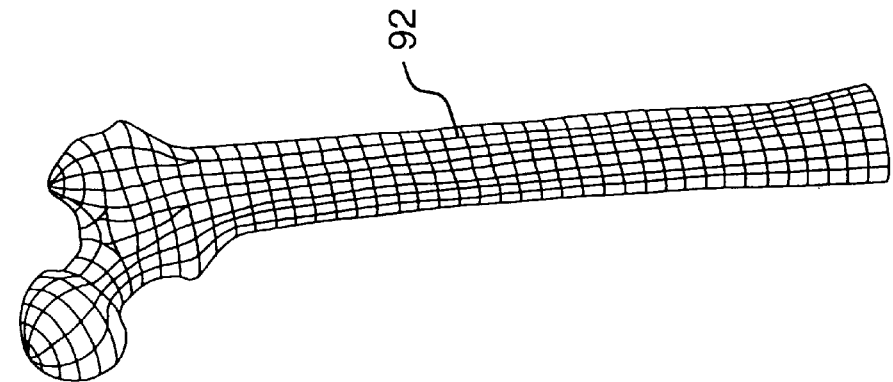
FIGS. 5(a–c) show the creation of the femur model using two dimensional scans of the femur (a), from which skeletal geometric data is extracted as shown in (b) and used to create the femur model (c)
Figure 5B:
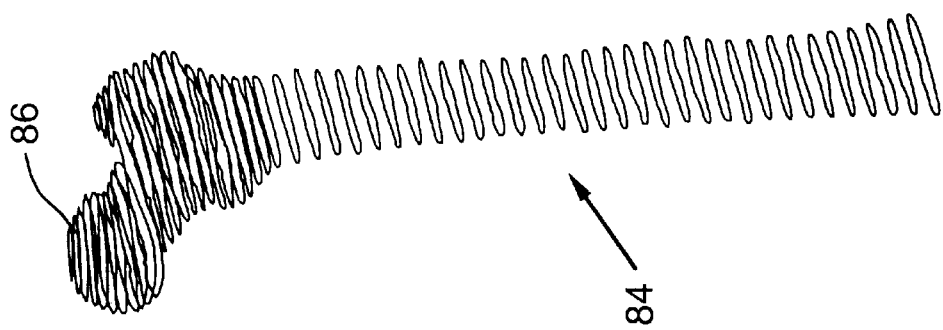
Figure 5A:
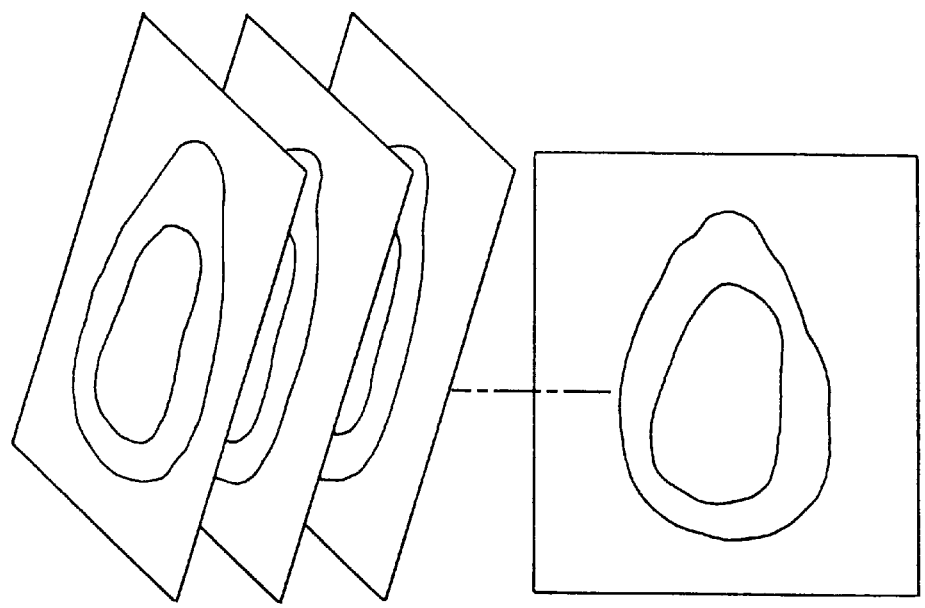

The operation of the apparatus 10 will now be discussed with reference to its use in a THR procedure. Generally, an acetabular cup 70 (FIG. 8) having a cup liner 72 in a convex portion thereof is implanted in an acetabulum 74 (FIG. 4*b*) of a pelvis 76. In addition, a femoral implant 78 (FIG. 7) having a head, or ball, 80 and a neck, or shaft, 82 is implanted into a femur 84. The femur 84 has a head portion 86 (FIG. 5) that is removed to facilitate the implantation. A bore 88 is drilled in the femur 84 into which the femoral implant 78 is placed. The femoral neck 82 is secured in the bore 88 in a position to allow the femoral head 80 to cooperate with the cup liner 72 in the acetabular cup 70.

In accordance with step 40, skeletal structure data is obtained on the femur and pelvic regions of the patient, preferably via CT scans as shown in FIG. 4(*a*) and 5(*a*), respectively, from the skeletal data source 13. The CT scans are either manually or automatically inputted in the computer system 20 (FIGS. 4(*b*) and 5(*b*)) and used to create geometric surface models 90 and 92 of the patient's pelvis 76 and femur 84 (FIGS. 4(*c*) and 5(*c*)), respectively as per step 42.

Figure 6:
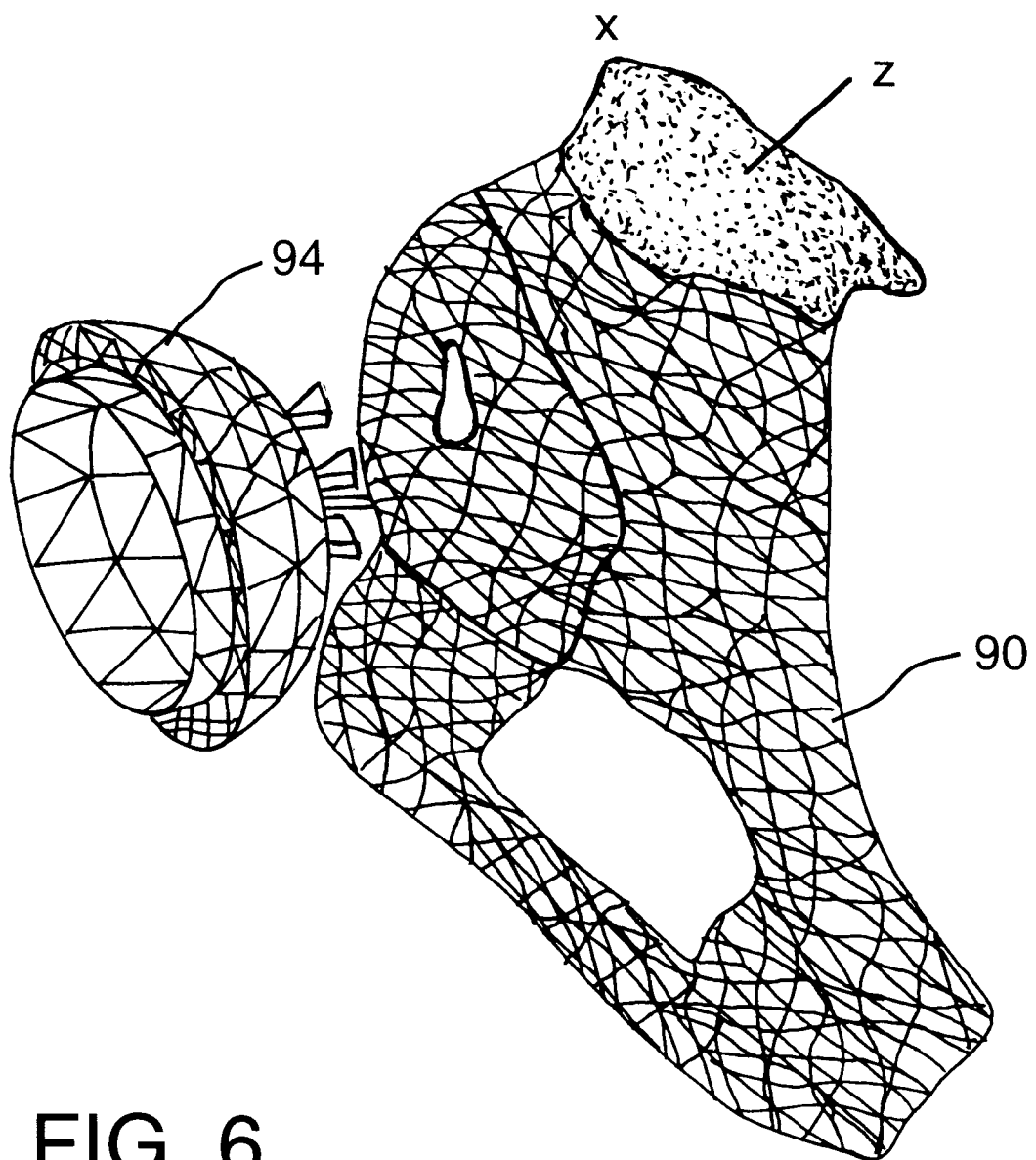
FIG. 6 shows the sizing of the acetabular cup in the pelvic model.
Figure 7:
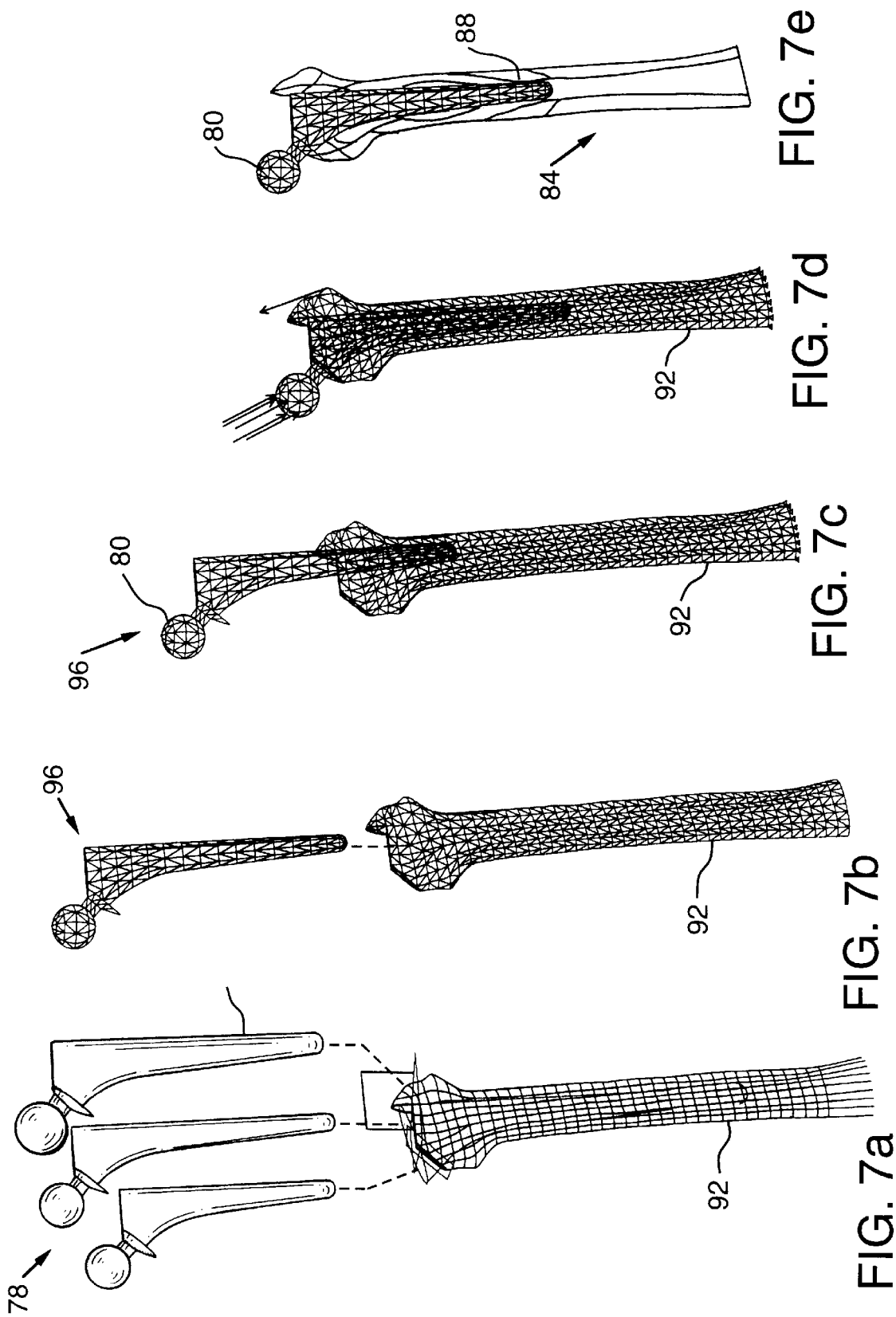
FIGS. 7(a–e) show the creation of different sized femoral implant models (a) and the fitting of the femoral implant model into a cut femur (b–e)

Geometric models 94 and 96 of the acetabular cup 70 and an femoral implant 78, shown in FIGS. 6 and 7, respectively, are created either manually or in an automated fashion using conventional computer assisted design modelling techniques with implant design or manufacturing data. The size of the acetabular cup 70 can be determined automatically based on the size of the acetabulum 74 determined from the pelvis model 90, the skeletal data or can be manually input. Similarly, the femoral implant 78 can be manually sized to cooperate with the selected acetabular cup 70 using standard implant components or the sizing of the head 80 and neck 82 of the femoral implant 78 can be customized to fit the femur 84 using the femoral implant model 96 and the femur model 92 as shown in FIGS. 7(*a–e*). One skilled in the art will appreciate that the computer system 20 in performing step 42 can be programmed using separate or combined software routines to create the geometric surface models of the patient's anatomy and the implant components.

The computer system 20 uses the geometric model 90 of the patient's pelvis 76, the model 92 of the patient's femur, the model 94 of the acetabular cup 70, and model 96 of the femoral implant 78 to perform simulated biomechanical testing of the acetabular cup 70 and the femoral implant 78 implanted at various test positions in the acetabulum 74 and femur 84, respectively, according to step 44. For example, in the case of femoral neck 82—cup liner 72 impingement, shown in FIG. 8, the important parameters in evaluating the prosthetic range of motion are the head 80 to neck 82 ratio of the femoral implant 78, the position, including angular orientation, of the acetabular cup 70 and the relative position of the femoral implant 78 with respect to the cup 70.

Figure 8:
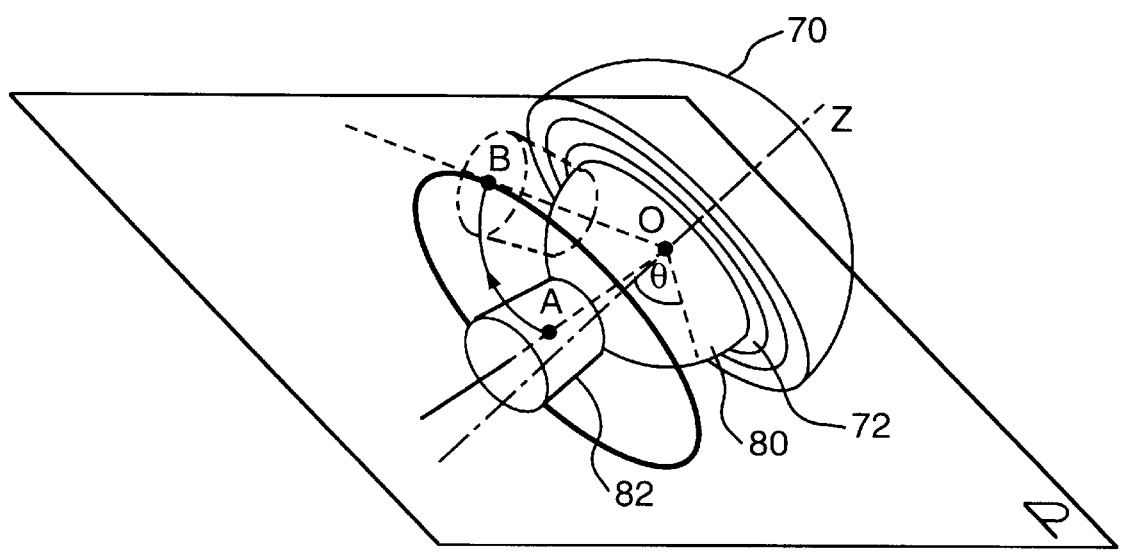
FIG. 8 is a schematic drawing showing the range of motion of a femoral shaft and the impingement (in dotted lines) of a femoral shaft on an acetabular cup.

While the present invention is applicable to non-axisymmetric acetabular implants (i.e. hooded liners, non-neutral liners) and femoral necks (i.e. non-symmetric cross sections), the following discussion of an axisymmetric acetabular cup and femoral neck alignment case is presented to ease the explanation of the concepts. If the center of rotation in the acetabular cup 70 coincides with the center of the head 80 of the femoral implant 78, as shown in FIG. 8, the angle $\Theta$ between the axis of symmetry Z of the acetabular cup 70 and the line of impingement OB defines the allowable angle of motion. The limits of impingement create a cone within which the axis of the femoral neck (line OA) can move without the femoral neck impinging upon the cup liner 72.

The position of the neck axis with respect to the cone can be evaluated by observing its intersection with a plane P placed at an arbitrary distance normal to the Z axis. The cross section of the cone defines the impingement circle (if, as stated above, both the liner 72 and the neck 82 are axisymmetric), and the path of the axis of the femoral neck 82 defines a curve in the plane P. In FIG. 8, the axis of the femoral neck 82 begins at point A and moves along the path AB to point B at which point the femoral neck 82 impinges upon the cup liner 72.

Figure 9B:
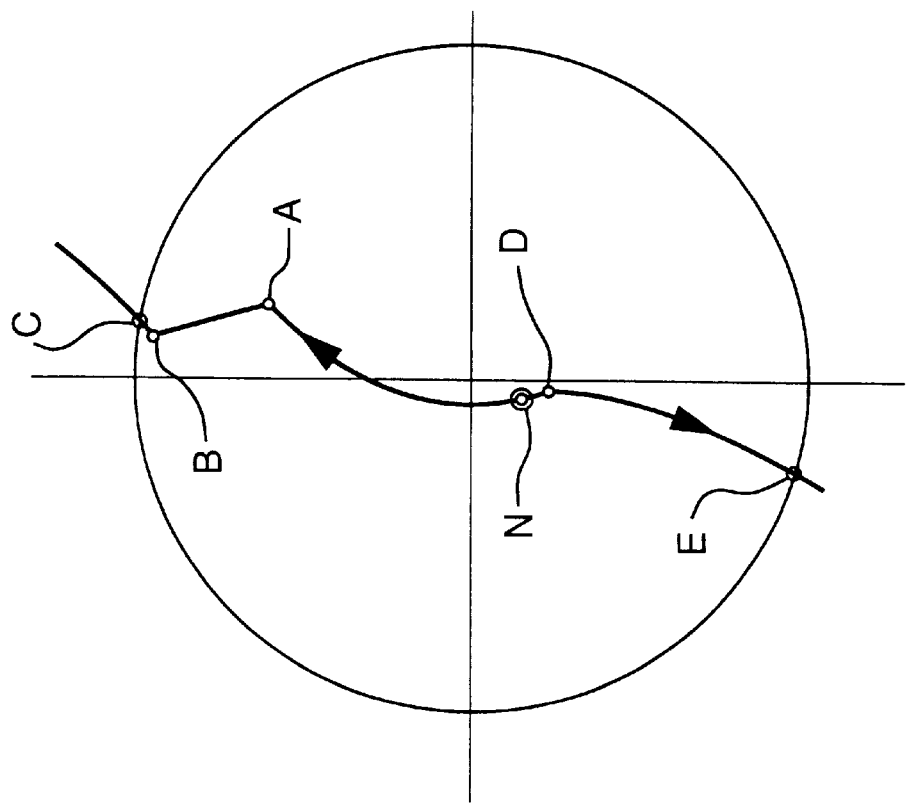
FIGS. 9(a–b) show the range of motion results from biomechanical simulation of two respective acetabular cup orientations.
Figure 9A:
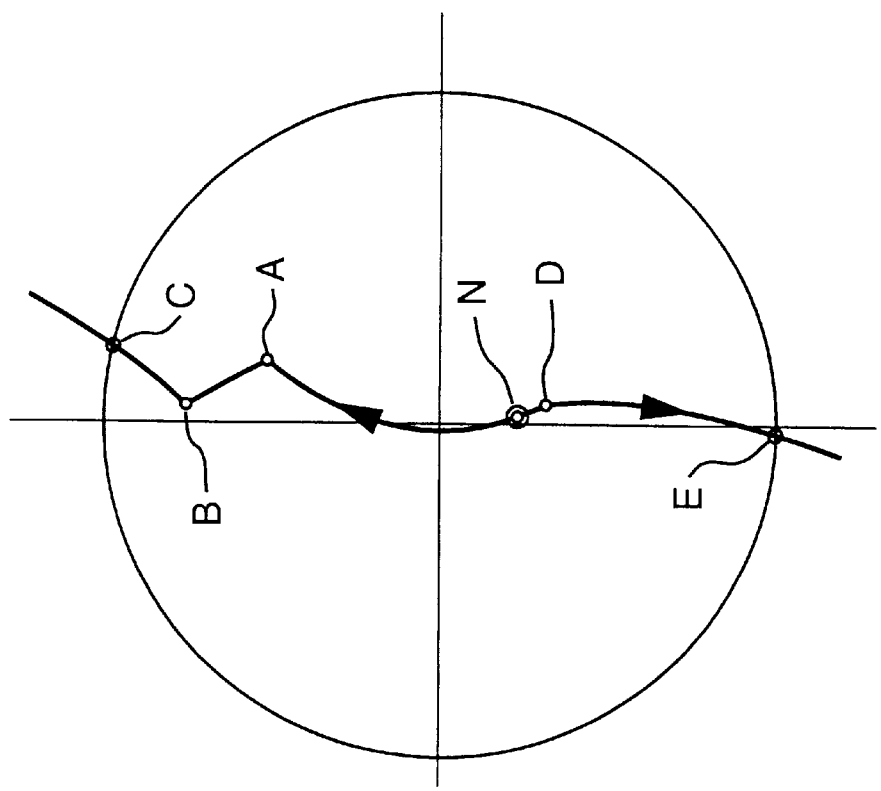

The motion of the femoral neck 82 can be derived from (and expressed as a function of) the physiological movement of the leg, described in terms of combined flexion, extension, abduction, adduction, and external and internal rotation. FIGS. 9(*a*) and 9(*b*) show an example of range of motion (ROM) simulation for two different cup orientations and for two identical sets of ROM exercises: (I) 90° flexion (A)+15° adduction (B)+maximum internal rotation (C) and (II) 10° extension (D)+maximum external rotation (E). As a result of reorienting the cup from 45° abduction+15° flexion (FIG. 9(*a*)) to 50° abduction+5° flexion (FIG. 9(*b*)), maximum internal rotation at the impingement point C is reduced from 15.7° to 4.3° in exercise I and maximum external rotation at the impingement point E is increased from 45.8° to 55.8° in the exercise II. In accordance with step 48, the implant position is determined by comparison of the calculated range of motion of the femoral implant 78 in the acetabular cup 70 with the predetermined range of motion. See "Simulation of Implant Impingement and Dislocation in Total Hip Replacement", Jaramaz et al., Computer Assisted Radiology, $10^{th}$ International Symposium and Exhibition, Paris, June, 1996, which is incorporated herein by reference.

In the execution of the intra-operative procedure 60, the implant position is identified in the pelvic model 90 prior to surgery as in step 52. During the surgical procedure, the pelvis 76 of the patient is exposed. One of the tracking targets 34, a pelvic target, is attached to the pelvic region, as shown in FIG. 3. Preferably, the target 34 is attached in close proximity to the acetabulum 74 to provide data as close to the area of interest as possible without becoming an impediment to the surgical procedure. The close proximate placement of the target 34 provides an additional benefit of minimizing the extent to which the pelvis must be exposed during the procedure. Positional data from discrete locations on the patient's pelvis 76 and femur 84 are taken and provided as input to the navigational guidance software 16 according to step 54.

Figure 10A:
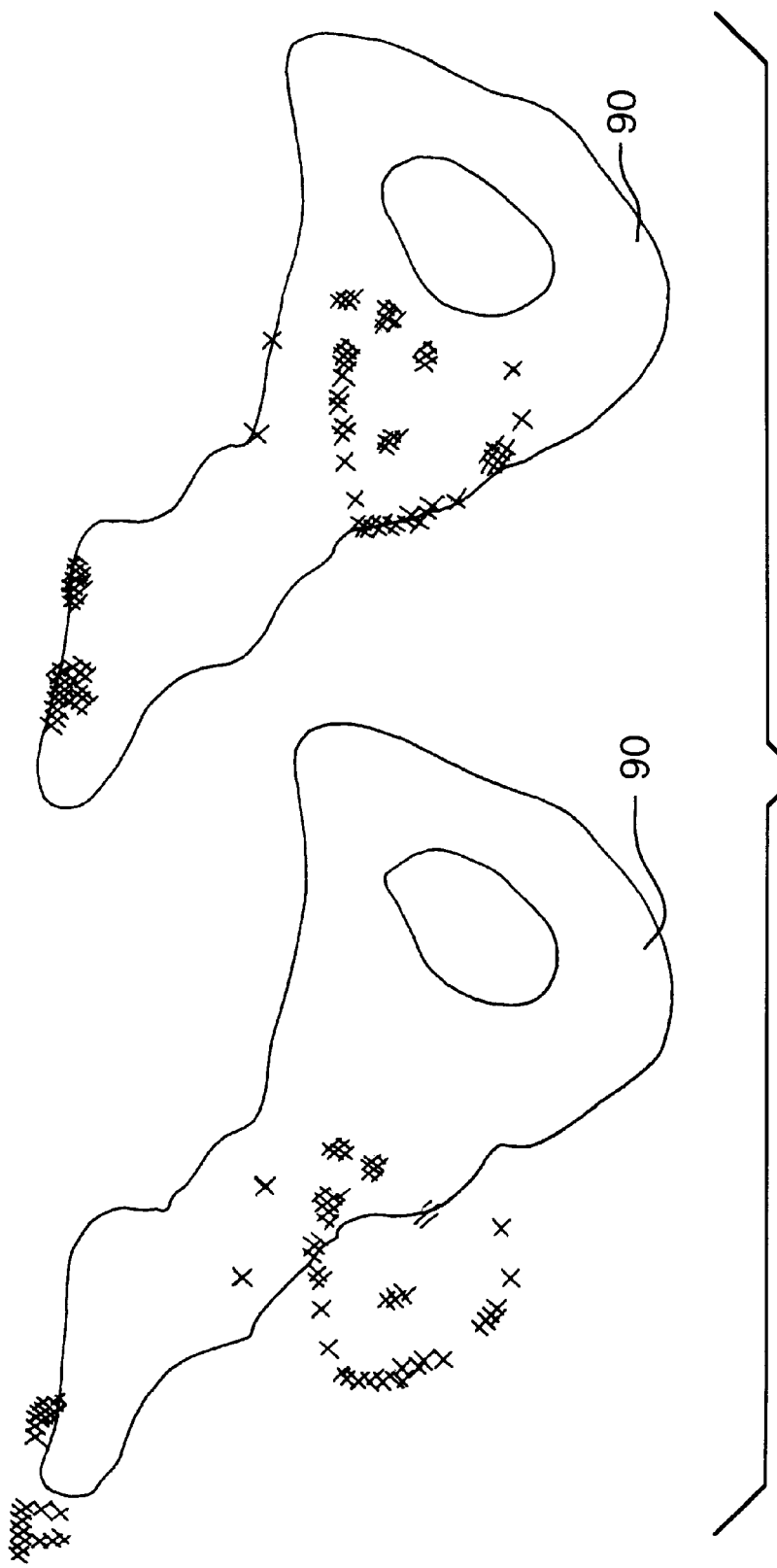
FIGS. 10(a) and (b) show the registration of the pelvis and femur.
Figure 10B:
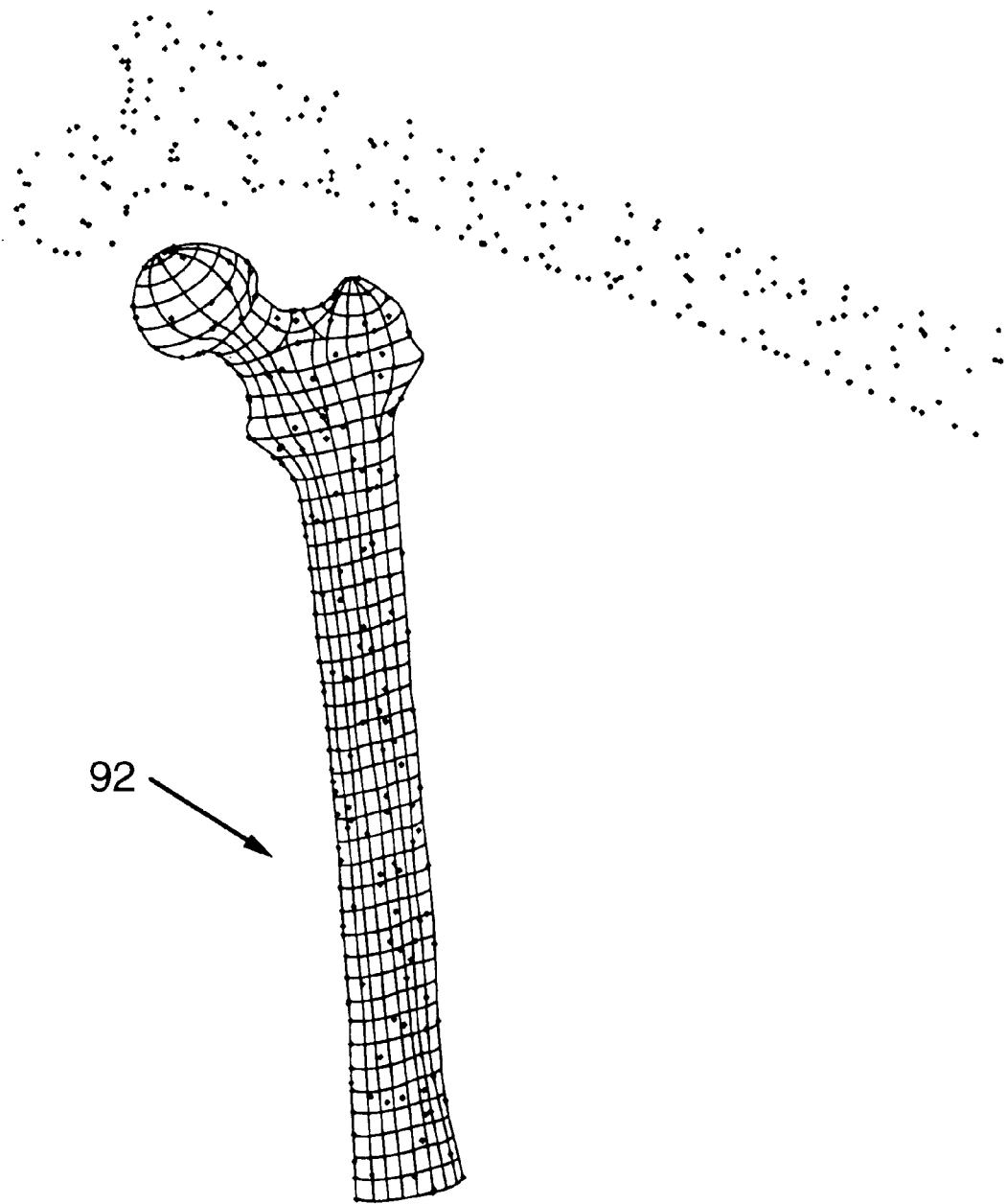

The intra-operative positional data is registered with the pelvic model 90 and femur model 92, as shown in FIGS. 10(*a*) and (*b*), to align the models with the intra-operative position of the patient's pelvis 76 and femur 84, respectively. During the acquisition of discrete registration point positional data from the pelvis 76, the tracking device 30, via camera 32, is used to track the pelvic target. The pelvic target position data is used in combination with the transformation developed using the registration data provide a spatial correspondence between pre-operative CT coordinates (i.e. pelvic model) and the intra-operative coordinates (i.e. measurements of the patient's pelvis relative to the pelvic target). Intra-operative tracking of the acetabular cup 70 is also performed relative to the pelvic target.

The position of the acetabular cup 70 prior to implantation is preferably tracked by attaching at least one other tracking target 34, a second target, to a cup insertion tool 98, as shown in FIG. 3, and mathematically relating the position of the second target 34 to the position of the cup 70. In this manner, the potential for damage to the cup 70 from directly mounting the target 34 to the cup 70 is eliminated. In addition, the target 34 can be placed on the tool 98 so as to not obscure the medical practitioner's view of the surgical area. Preferably, a third, or reference, target 34 is positioned to allow for spatial orientation of the operating room.

Guidance in the placement of the acetabular cup 70 is provided by the navigational software 16 in the computer 20 which displays on the monitor 22 near real time position tracking of the cup 70 relative to the to the pre-operatively specified implant position. Once the cup 70 is aligned with the implant position, the cup 70 is in the pre-operatively planned orientation.

A series of tests were developed and performed to assess the ability of the apparatus 10 to correctly predict the impingement of the femoral neck 82 with acetabular cup liner 72. The series of tests were developed because the testing described in available references did not include experimental parameters, such as neck size and the orientation of the fomeral neck axis, necessary to evaluate the biomechanical simulator. The testing was performed using a laboratory prototype of the apparatus 10, known as the HipNaV™ system. Details of the testing are presented in Jaramaz et al., "Range of Motion After Total Hip Arthroplasty: Experimental Verification of the Analytical Simulator", Carnegie Mellon University, Robotics Institute Technical Report CMU-RI-TR-97-09 (February 1997) and Jaramaz et al., "Simulation of Implant Impingement and Dislocation in Total Hip Replacement", Computer Assisted Radiology, $10^{th}$ International Symposium and Exhibition, Paris, June, 1996, both of which are incorporated herein by reference.

Figures 11A, 11B:
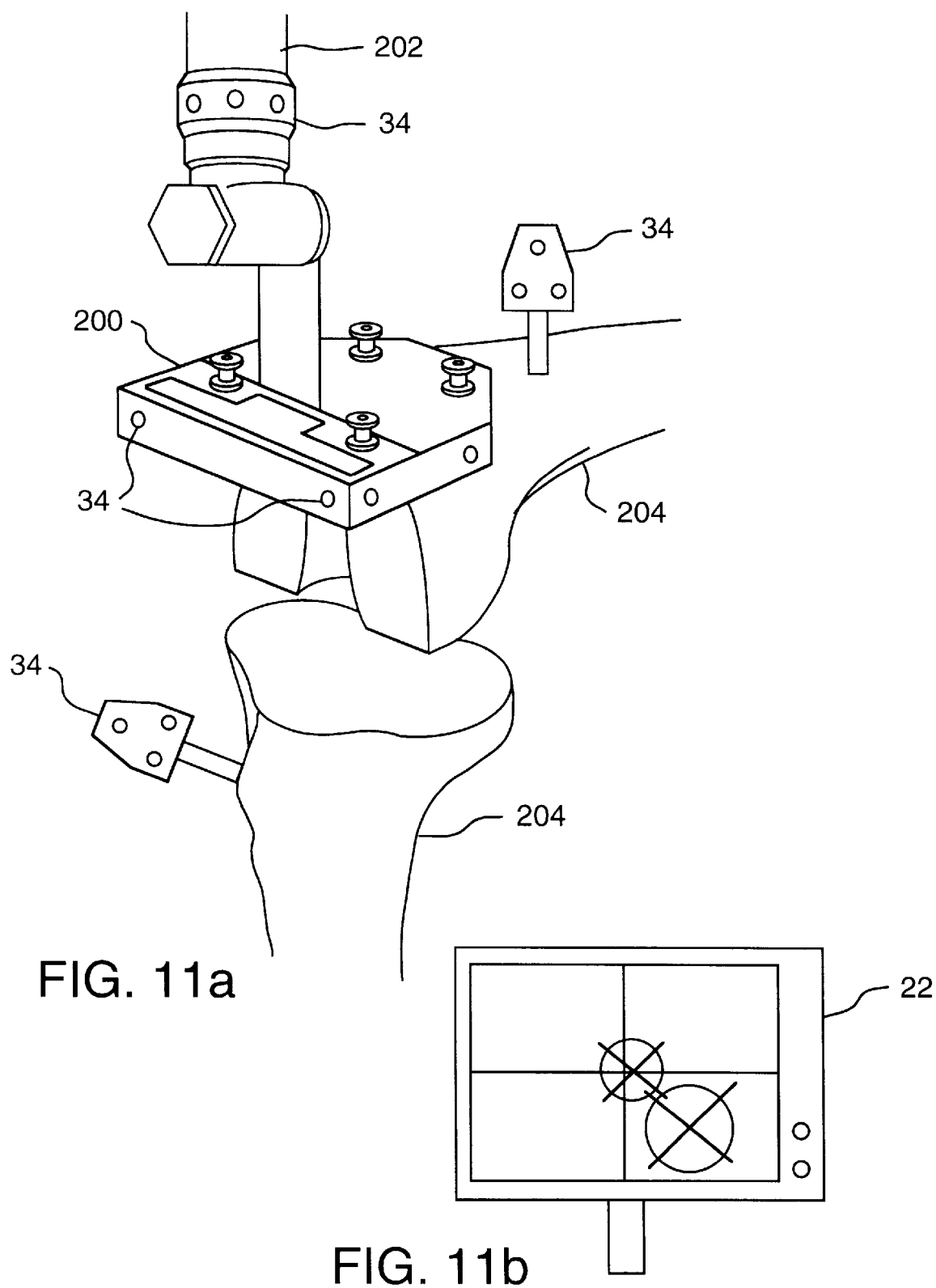
FIGS. 11(a) and (b) show an image guided total knee arthroplasty.

FIGS. 11(*a*) and (*b*) show an image guided total knee arthroplasty. In FIG. 11(*a*) it can be seen that the targets 34 are attached to a guide 200, a tool 202, and the bones of interest 204. After registration, the position of the guide 200, the tool 202, the bones 204, and any other instruments are continuously tracked in space. As shown in FIG. 11(*b*), the position of the guide 200 and the tool 202 are continuously tracked and guided using the display monitor 22 according to the preoperative plan, which is developed as described hereinabove.

Figure 12A:
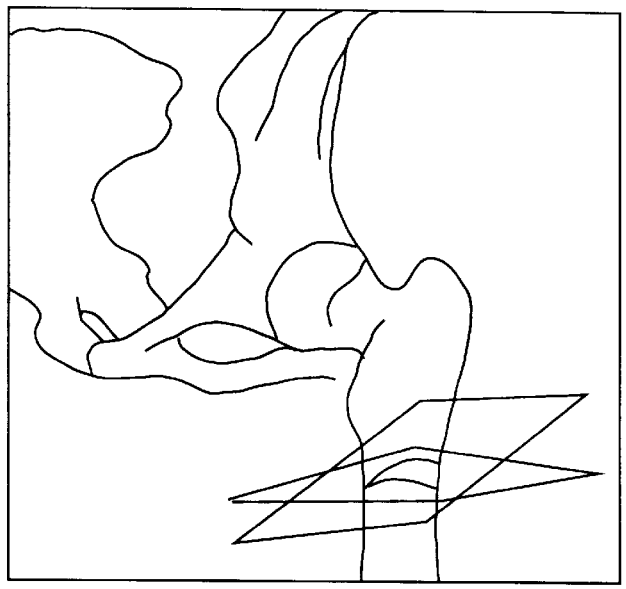
FIGS. 12(a–c) show the planning of a femoral osteotomy.
Figure 12B:
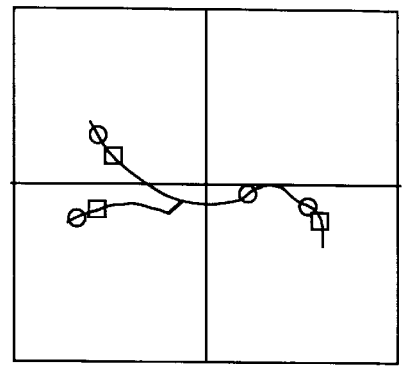
Figure 12C:
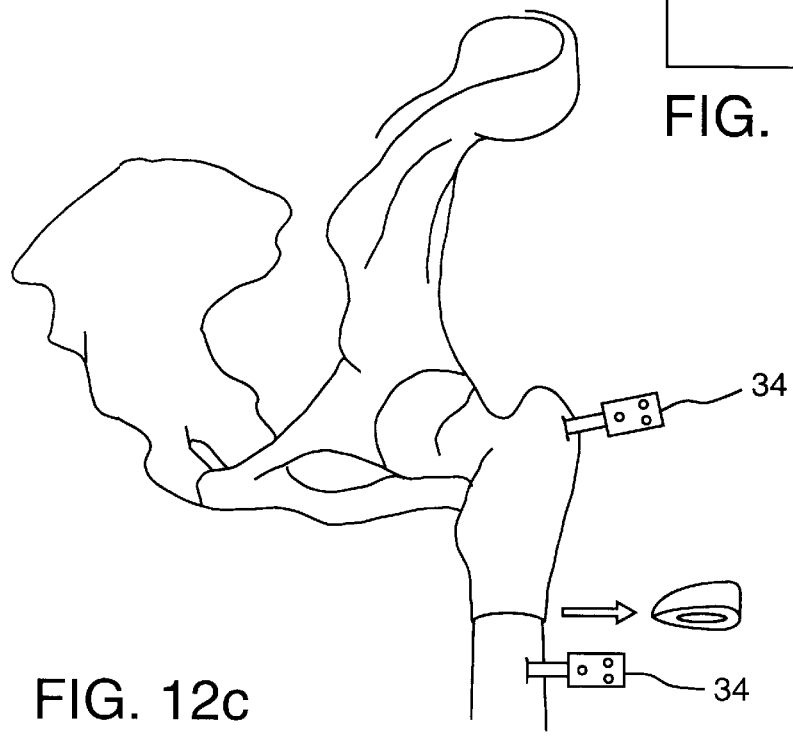

FIGS. 12 (*a*–*c*) show the planning of a femoral osteotomy. FIG. 12(*a*) illustrates how the bone cutting planes are pre-operatively positioned and rotated interactively using the techniques of the present invention. FIG. 12(*b*) illustrates the process of the pre-operative kinematic biomechanical simulator 14, which calculates the range of motion for selected test motions. FIG. 12(*c*) illustrates how the bone fragments and tools are tracked and bone segments are repositioned intra-operatively using the techniques of the present invention.

Although the present invention has been described hereinabove with specific examples directed to hip replacement and revision, knee arthroplasty, and femoral osteotomy, the methods and apparatuses may be employed in a variety of procedures including joint replacement with artificial implants, osteochondral grafts (from a cadaver or tissue engineered), and osteotomy. The methods and apparatuses may be used in hand and wrist joint replacements and revisions such as replacement and arthroplasty of the proximal interphalangeal joint, replacement and arthroplasty of the metacarpophalangeal joint, replacement and arthroplasty of the thumb axis, and replacement and arthroplasty of the wrist. The procedures and apparatuses are also applicable to elbow joint replacements and revisions such as resurfacing elbow replacement, and shoulder joint replacements and revisions such as shoulder arthroplasty. Also, the hip replacement and revision procedures to which the techniques and apparatuses of the present invention may be applied include total hip replacement and arthroplasty, revision total hip replacement and arthroplasty, acetabular and pelvic osteotomies, proximal femoral osteotomy, arthrodesis, and joint resurfacing with osteochondral grafts and cartilage transplant procedures. The methods and apparatuses of the present invention may also be used in knee joint replacement and revision procedures such as total knee replacement and arthroplasty, revision total knee replacement and arthroplasty, unicompartmental total knee replacement and arthroplasty, tibial osteotomy, anterior cruciate ligament reconstruction, posterior cruciate ligament reconstruction, and osteochondral resurfacing and cartilage transplant procedures. The procedures and apparatuses of the present invention are applicable to foot and ankle joint replacement and revision procedures such as ankle replacement arthroplasty, ankle arthrodesis, midfoot reconstruction, arthroplasty of the great toe, and arthroplasty of lesser toes. The techniques and apparatuses of the present invention are applicable to spine procedures such as nucleus pulposus disc replacements.

What is claimed is:

1. An apparatus for facilitating the implantation of an artificial component in one of a hip joint, a knee joint, a hand and wrist joint, an elbow joint, a shoulder joint, and a foot and ankle joint, comprising:

a pre-operative geometric planner; and a pre-operative kinematic biomechanical simulator in communication with said pre-operative geometric planner wherein said pre-operative geometric planner outputs at least one geometric model of the joint and the pre-operative kinematic biomechanical simulator outputs a position for implantation of the artificial component.

2. The apparatus of claim 1, further comprising an intra-operative navigational module in communication with said pre-operative kinematic biomechanical simulator.

3. The apparatus of claim 2, further comprising a tracking device in communication with said intra-operative navigational module.

4. The apparatus of claim 1, wherein said pre-operative geometric planner is responsive to a skeletal data source.

5. The apparatus of claim 4, wherein said skeletal data source includes geometric data.

6. The apparatus of claim 4, wherein said pre-operative geometric planner outputs at least one geometric model of the component.

7. The apparatus of claim 6, wherein said pre-operative kinematic biomechanical simulator is responsive to said geometric model and outputs an implant position.

8. The apparatus of claim 7, wherein said implant position includes an angular orientation of the component.

9. The apparatus of claim 3, wherein said tracking device is selected from the group consisting of an acoustic tracking system, shape based recognition tracking system, video-based tracking system, mechanical tracking system, electromagnetic tracking system and radio frequency tracking system.

10. A system for facilitating an implant position for at least one artificial component in one of a hip joint, a knee joint, a hand and wrist joint, an elbow joint, a shoulder joint, and a foot and ankle joint, comprising:

a computer system including;
  a pre-operative geometric planner; and
  a pre-operative kinematic biomechanical simulator in communication with said pre-operative geometric planner wherein pre-operative geometric planner outputs at least one geometric model of the joint and the pre-operative kinematic biomechanical simulator outputs a position for implantation of the artificial component; and a tracking device in communication with said computer system.

11. The system of claim 10, further comprising at least one display monitor in communication with said computer system.

12. The system of claim 10, further comprising at least one controller in communication with said computer system.

13. The system of claim 10, wherein said tracking device includes at least one camera.

14. The system of claim 10, wherein said tracking device includes at least one target.

15. The system of claim 10, wherein said computer system further includes an intra-operative navigational module in communication with said pre-operative kinematic biomechanical simulator.

16. The system of claim 10, further comprising:

a robotic device in communication with said computer system; and a surgical tool connected to said robotic device.

17. A computerized method of facilitating the implantation of an artificial implant in one of a hip joint, a knee joint, a hand and wrist joint, an elbow joint, a shoulder joint, and a foot and ankle joint, comprising:

creating a three dimensional bone model based on skeletal geometric data of a bone and a bony cavity into which the artificial implant is to be implanted;

creating a three dimensional component model of the artificial implant;

simulating movement of the joint with the artificial implant in a test position;

calculating a range of motion of the artificial implant and the bones comprising the joint for the test position based on the simulated movement;

determining an implant position based on a predetermined range of motion and the calculated range of motion;

identifying the implant position in the bone model;

aligning the bone model with the patient's bone and placing the implant based on positional tracking data providing the position of the implant and the bone; and tracking the implant and the bone to maintain alignment of the bone model and to determine the position of the implant relative to the bone.

* * * * *